US008741949B2

(12) United States Patent
Nieland

(10) Patent No.: US 8,741,949 B2
(45) Date of Patent: Jun. 3, 2014

(54) INHIBITORS OF CARNITIN-PALMITOYL-TRANFERASE-1 FOR THE TREATMENT AND PREVENTION OF DISORDERS CAUSED BY DELIPIDATION OF NEURAL TISSUE

(75) Inventor: Josephus Dirk Nieland, Arthus C (DK)

(73) Assignee: Meta-IQ ApS, Aarhus C (DK)

( * ) Notice: Subject to any disclaimer, the term of this patent is extended or adjusted under 35 U.S.C. 154(b) by 232 days.

(21) Appl. No.: 13/001,422

(22) PCT Filed: Jun. 25, 2009

(86) PCT No.: PCT/EP2009/057983
§ 371 (c)(1), (2), (4) Date: Mar. 22, 2011

(87) PCT Pub. No.: WO2009/156479
PCT Pub. Date: Dec. 30, 2009

(65) Prior Publication Data

US 2011/0178172 A1 Jul. 21, 2011

Related U.S. Application Data

(60) Provisional application No. 61/076,316, filed on Jun. 27, 2008.

(51) Int. Cl.
*A61K 31/335* (2006.01)
*A61K 31/19* (2006.01)

(52) U.S. Cl.
USPC .......... 514/475; 514/557; 514/903

(58) Field of Classification Search
USPC .......... 514/475, 557, 903
See application file for complete search history.

(56) References Cited

U.S. PATENT DOCUMENTS

2010/0286073 A1* 11/2010 Jenkins .......... 514/26

FOREIGN PATENT DOCUMENTS

| | | | |
|---|---|---|---|
| EP | 0046590 | B1 | 3/1982 |
| EP | 0916336 | A1 | 5/1999 |
| WO | 97/11689 | | 4/1997 |
| WO | 97/35564 | | 10/1997 |
| WO | 98/23291 | | 6/1998 |
| WO | 03/037323 | A2 | 8/2003 |
| WO | 2004/111199 | A2 | 12/2004 |
| WO | 2007116074 | A1 | 10/2007 |
| WO | 2009044202 | A1 | 9/2009 |

OTHER PUBLICATIONS

Bristow, Michael. "Etomoxir: a new approach to treatment of chronic heart failure". The Lancet vol. 356, 2000, pp. 1621-1622.*
Dutta et al. "Pathogenesis of axonal and neuronal damage in multiple sclerosis". Neurology 2007: 68 (Suppl 3):S22-S31.*
Sanchez C. et al. "R-citalopram conuteracts the effect of R-citalopram in a rat conditionerd fear stress model of anxiety" Pharmacol. Biochem: Behav: 2003; 75 (4):903-907.
Excerpt from Jes Gerlach: Depression ISDN 87-90420-48-9; p. 164 and English translation thereof.
Giamberardino M.A. "Update on Fibromyalgia Syndrome" Pain Clinical Updates vol. XVI, Issue 4, 2008.
International Search Report in corresponding PCT/EP2009/057983 dated Sep. 12, 2009.
Suzer et al., "Lipid peroxidation and glutathione levels after cortical injection of ferric chloride in rats: effect of trimetazidine and deferoxamine", Research in Experimental Medicine, vol. 199, No. 4, pp. 223-229, Feb. 2000, Springer-Verlag 2000.
R. Grangier et al., "Neuropathie optique hereditaire de Leber. Mutations de Wallace du genome mitochondrial. A propos de 3 cas familiaux" Bulletin des Societes D'Ophtalmologie de France, vol. 95, No. 6, pp. 413-417.
Dogen H. et al., "The Usefulness of Trimetazidine Hydrochloride, Prostaglantine E1 and Aldose Reductase Inhibitor (ONO-2235) in Diabetic Neropathy", Journal of the Japan Diabetes Society, vol. 29, suppl. No. 01, pp. 107-109, 1986.
Deschamps D. et al. "Inhibition by Perhexiline of Oxidative Phosphorylation and the Beta-Oxidation of Fatty Acids: Possible Role in Pseudoalcoholic Liver Lesions", Hepatology, vol. 19, No. 4, pp. 948-961, 1994.
Kennedy J. et al., "Inhibition of Carnitine Palmitoyltransferase-1 in Rat Heart and Liver by Perhexiline and Amiodarone", Biochemical Pharmacology, vol. 52, pp. 273-280, 1996.
Carregal M. et al., "Beneficial Effects of Oxfenicine on the Hypoxic Rat Atria", Archives of Physiology and Biochemistry, vol. 103, No. 1, pp. 45-49, 1995.
Kennedy J. et al., Effect of Perhexiline and Oxfenicine on Myocardial Function and Metabolism During Low-Flow Ischemia/Reperfusion in the Isolated Rat Heart, Journal of Cardiovascular Pharmacology, vol. 36, No. 6, pp. 794-801, Dec. 2000.
Swithers S., "Development of independent ingestive responding to blockade of fatty acid oxidation in rats", Am J Physiol Regul Integr Comp Physiol, vol. 273, pp. R1649-R1656, 1997.
Friedman M. et al., "Fuel partitioning and food intake: role for mitochondrial fatty acid transport", Am J. Physiol, vol. 258, pp. R216-R221, Jan. 1990.
Seitelberger R. et al., "Effects of Acylcarnitine Transferase Blocade on Metabolism and Function in the Normally and Underperfused Canine Myocardium", J. Clin. Chem.. Clin. Biochem, vol. 28, No. 5, pp. 341-346, May 1990.
Reinauer H. et al., "Influence of Carnitine Acyltransferase Inhibitors on the Performance and Metabolism of Rat Cardiac Muscle", J. Clin. Chem. Clin. Biochem, vol. 28, No. 5, pp. 335-339, May 1990.
Skorin C. et al., "Peroxisomal fatty acid oxidation and inhibitors of the mitochondrial carnitine palmitoyltransferase I in isolated rat hepatocytes", Biochem J, vol. 281, pp. 561-567, Jan. 1992.
Tuman, R. et al., "Effect of the Fatty Acid Oxidation inhibitor 2-Tetradecylglycidic Acid (TDGA) on Glucose and Fatty Acid Oxidation in Isolated Rat Soleus Muscle", Int. J. Biochem., vol. 20, No. 2, pp. 155-160, 1988.
Prip-Buus C. et al., "Evidence that the sensitivity of carnitine palmitoyltransferase I to inhibition by malonyl-CoA is an important site of regulation of hepatic fatty acid oxidation in the fetal and newborn rabbit—Perinatal development and effects of pancreatic hormones in cultured rabbit hepatocytes", Biochem. J, vol. 269, pp. 409-415, Jul. 1990.

(Continued)

*Primary Examiner* — Renee Claytor
(74) *Attorney, Agent, or Firm* — Roberts Mlotkowski Safran & Cole, P.C.

(57) ABSTRACT

Carnitin-Palmitoyl-Transferase-1 (CPT-1) inhibitor for use in treating and/or preventing disorders caused by delipidation of neural tissue.

16 Claims, 6 Drawing Sheets

(56) References Cited

OTHER PUBLICATIONS

Winder, W. W., "Malonyl-CoA—Regulator of Fatty Acid Oxidation in Muscle During Exercise", Exerc Sport Sci Rev, vol. 26, pp. 117-132, 1988.
Lopaschuk G. et al., "The 1993 Merck Frosst Award. Acetyl-CoA carboxylase: an important regulator of fatty acid oxidation in the heart", Can J Physiol Pharmacol, vol. 72, No. 10, pp. 1101-1109,1994.
Pizer E. et al., "Malonyl-Coenzyme-A Is a Potential Mediator of Cytotoxicity Induced by Fatty-Acid Synthase Inhibition in Human Breast Cancer Cells and Xenografts1", Cancer Research, vol. 60, pp. 213-218, Jan. 2000.
Thupari J. et al., "Fatty Acid Synthase Inhibition in Human Breast Cancer Cells Leads to Malonyl-CoA-Induced Inhibition of Fatty Acid Oxidation and Cytotoxicity"., Biochem Biophys Res Commun, vol. 285, pp. 217-223, 2001.
Brunmark C. et al., "The new orally active immunoregulator laquinimod (ABR-215062) effectively inhibits development and relapses of experimental autoimmune encephalomyelitis", Journal of Neuroimmunology, vol. 130, pp. 163-172, 2002.
Lucas G., et al., "Serotonin4 (5-HT4) Receptor Agonists Are Putative Antidepressants with a Rapid Onset of Action", Neuron, vol. 55, pp. 712-725, 2007.
Kurnellas M. et al., "Mechanisms of neuronal damage in multiple sclerosis and its animal models: role of calcium pumps and exchangers", Biochem Soc Trans, vol. 35, pp. 923-926, 2007.
Tabor M. P. et al., "An Advanced In Vitro Model to Study Hypoxia/Low Glucose-Induced Neuronal Cell Damage and Death", Annals of the New York Academy of Sciences, vol. 825, No. 1, pp. 267-278, 1997.
Gartlon J. et al., "Evaluation of a proposed in vitro test strategy using neuronal and non-neuronal cell systems for detecting neurotoxicity", Toxicology in Vitro, vol. 20, No. 8, pp. 1569-1581, 2006.
Written Opinion of the International Searching Authority of PCT/EP2009/057983.
International Preliminary Report on Patentability of PCT/EP20091057983 dated Jan. 5, 2011.
Ponomarev E. et al., "yo T Cells Regulate the Extent and Duration of Inflammation in the Central Nervous System by a Fas Ligand-Dependent Mechanism" The Journal of Immunology, 2005, 174, pp. 4678-4687.
"Inhibition of fatty acid metabolism ameliorates disease activity in an animal model of multiple sclerosis" Leah P. Shriver & Marianne Manchester; Skaggs School of Pharmacy and Pharmaceutical Sciences, University of California, San Diego, CA Scientific Reports 1:7 DOI:10.1038/srep00079 published Sep. 1, 2011.
Jerjes, et al., "Diurnal Patterns of Salivary Cortisol and Cortisone Output in Chronic Fatigue Syndrome", Journal of Affective Disorders, 87, 2005, pp. 299-304.
Linkowski, et al., "The 24-hour Profile of Adrenocorticotropin and Cortisol in Major Depressive Illness", J. Clin. Endocrinol. Metab., 1985, 1 page.

* cited by examiner

INHIBITORS OF CARNITIN-PALMITOYL-TRANFERASE-1 FOR THE TREATMENT AND PREVENTION OF DISORDERS CAUSED BY DELIPIDATION OF NEURAL TISSUE

CROSS-REFERENCE TO RELATED APPLICATIONS

The present Application is a U.S. national phase of PCT/EP2009/057983 filed on Jun. 25, 2009 ("PCT Application"), which claims priority from U.S. Provisional Application No. 61/076,316 filed on Jun, 27, 2008, both of which are hereby incorporated by reference in their entirety into the present Application.

The present invention relates to the identification of therapeutic methods and pharmaceutical compositions for the prophylaxis and/or the treatment of disorders caused by delipidation of neural tissue. In particular it has been found that a number of severe mental and neurological diseases are caused by or are related to delipidation of neural tissue and in particular delipidation of myelin sheets. It has know been found that these severe diseases can be effectively treated or prevented by blocking of the enzyme Carnitin-Palmitoyl-Transferase-1 (CPT-1).

Mental and neurological diseases disorders affect between 10 and 15% of the human population, often leading to social isolation or suicide. Examples of mental disorders include Depression and impairment of recent and remote memory (loss of short and long term memory). Many neurological disorders result in impairment of the control of the body, e.g. as seen in Multiple sclerosis (MS).

A variety of mechanisms have been proposed to account for the generation of Mental and neurological disorders. No general model for the outbreak of these disorders has been established so far in the art. However, it is widely accepted that many of the mental and neurological disorders are triggered by stress or an inflammatory response induced by an infection with a viral or bacterial pathogen.

Ideally, treatments for mental and neurological disorders should be aimed at curing the disease. To date, this ideal has not been reached. Known treatments for the disorders are not cures, but merely palliatives, aimed at reducing symptoms to provide the patient with an acceptable quality of life or slowing down the progression of the disease. For example, the drugs that presently available for the treatment of depression take about 4 weeks before they start working and they work in maximally 50% of the patients. In memory impairment that can be induced by different diseases, like stress, there is no treatment. For multiple sclerosis the drugs on the market, can only slow down the progression of the disease. These therapies, which are relatively non-specific, have significant side-effects.

Consequently, the problem underlying the present invention resides in providing an improved therapy for the treatment of mental and neurological diseases.

The invention is described in detail below with reference to the appended figures.

Figure 1:
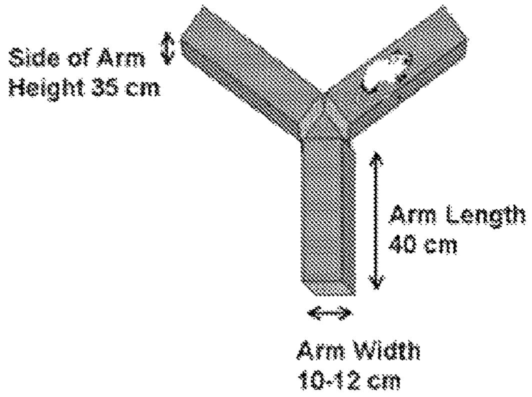
FIG. 1 is a diagram of a Y-maze used to assess the normal navigation behaviors of rodents.

The present invention is based on the unexpected finding that the inhibition of the enzyme Carnitin-Palmitoyl-Transferase-1 (CPT-1) elicits a positive effect on mental and neurological disorders. It could be shown that CPT-1, is upregulated in a number of highly different disorders (see Tables 1 and 2). Therefore, the present invention provides the possibility to prevent, alleviate or cure such disorders.

Without being bound to any theory, it is believed that a predisposition mediating the progression of these diseases involves fatty acid metabolism in neural tissue. Consequently, the mechanism of disease progression is considered to be the switch to fatty acid metabolism. Said regulation of metabolic pathways generates a vicious cycle that ends in delipidation of neural tissue and in particular myelin sheet destruction.

Neural tissue is specialized for the conduction of electrical impulses that convey information or instructions from one region of the body to another. About 98% of neural tissue is concentrated in the brain and spinal cord, the control centers for the nervous system. Myelin is a part of the neural tissue and is an electrically-insulating dielectric phospholipid layer that surrounds the axons of many neurons. Myelin made by different cell types varies in chemical composition and configuration, but performs the same insulating function. Myelinated axons are white in appearance, hence the "white matter" of the brain. Myelin is composed of about 80% lipid fat and about 20% protein. Some of the proteins that make up myelin are Myelin basic protein (MBP), Myelin oligodendrocyte glycoprotein (MOG), and Proteolipid protein (PLP). Myelin is made up primarily of a glycolipid called galactocerebroside.

Thus, in a first aspect of the invention, the above problem is solved by using Carnitin-Palmitoyl-Transferase-1 (CPT-1) inhibitor for treating and/or preventing disorders caused by delipidation of neural tissue.

As used herein the term "delipidation of neural tissue" is intended to mean the fatty acid oxidation of lipids that are located in the neural tissue, in particular the phospholipid layer that surrounds the axons of many neurons, i.e. the myelin sheet.

As used herein, the terms "CPT-1 inhibitor" or "inhibiting agent" refer to any compound capable of down-regulating, decreasing, reducing, suppressing, or inactivating the amount and/or activity of the enzyme Carnitin-Palmitoyl-Transferase-1 (CPT-1), which is a key enzyme of the fatty acid oxidation pathway, and has the following catalytic activity: Palnnitoyl-CoA+L-carnitine=CoA+L-palmitoylcarnitine. The enzyme is also known under the following synonyms: EC 2.3.1.21, CPT I, CPTI-L, Carnitine palmitoyltransferase 1A, Carnitine palmitoyltransferase 1B, Carnitine palmitoyltransferase 1C, CPT 1M. Generally, these CPT-1 inhibitors or inhibiting agents may be proteins, oligo- and polypeptides, nucleic acids, genes, and chemical molecules. Suitable protein inhibitors may be, for example, monoclonal or polyclonal antibodies which bind to one of the enzymes described below.

Inhibition of enzymes can be achieved by any of a variety of mechanisms known in the art, including, but not limited to, binding directly to the enzyme (e.g., enzyme inhibitor compound binding complex or substrate mimetic), denaturing or otherwise inactivating the enzyme, inhibiting the expression of a gene which encodes the enzyme (e.g., transcription to mRNA, translation to a nascent polypeptide) and/or final modifications to a mature protein.

As used herein, the term "inhibit" or "inhibiting" refer to any effect in down-regulating, decreasing, reducing, suppressing, or inactivating (also partially) the amount and/or activity of the Carnitin-Palmitoyl-Transferase-1 enzyme.

As used herein, the term "regulating the expression and/or activity" generally refers to any process that functions to control or modulate the quantity or activity (functionality) of a cellular component, particularly an enzyme. Static regulation maintains expression and/or activity at some given level. Up-regulation refers to a relative increase in expression and/or activity. Accordingly, down-regulation refers to a decrease in expression and/or activity. Down-regulation is synonymous with the inhibition of a given cellular component's expression and/or activity.

Suitable CPT-1 inhibitors can be identified by screening test compounds, or a library of test compounds, for their ability to inhibit the Carnitin-Palmitoyl-Transferase-1 activity. In this context, cells or cell lysates may be tested for their ability to degrade palmitate by incubating the cells or cell lysates with radioactive palmitate and measuring the production of radioactive ketone bodies and/or the release of $^{14}CO_2$. Furthermore, it is possible to perform an in silico screen, based on the structure of a known enzyme involved in fatty acid oxidation.

In preferred embodiments, the inhibitor inhibiting the expression and/or activity of the enzyme Carnitin-Palmitoyl-Transferase-1 (CPT-1) is an arylalkyl- and aryloxyalkyl-substituted oxirane carboxylic acid of the following formula I

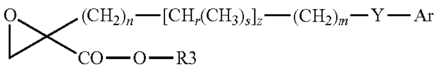

wherein

Ar is a substituted phenyl radical

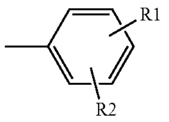

a 1- or 2-naphthyl radical which is substituted by a radical R4, or a heterocyclic radical Het;

R1 is a hydrogen atom, a halogen atom, or a 1-4 C lower alkyl group; a 1-4 C lower alkoxy group, a nitro group, or a trifluoromethyl group;

R2 is a hydrogen atom, a halogen atom, or a 1-4 C lower alkyl group; a 1-4 C lower alkoxy group, a nitro group, a trifluoromethyl group, a fully or predominantly fluorine-substituted 1-3 C alkoxy group or one of:

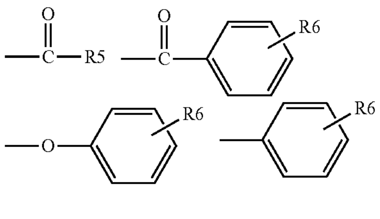

R3 is a hydrogen atom or a 1-4 C lower alkyl group;

R4 is a hydrogen atom, a 1-4 C lower alkyl group, an optionally fully or predominantly fluorine-substituted 1-3 C alkoxy group, or a halogen atom;

R5 is a 1-4 C lower alkyl group;

R6 is a hydrogen atom, a halogen atom, or a 1-4 C lower alkyl group;

Y is the grouping —O— or —$CH_2$—;

z is 0 or 1 s is 1 or 2 r is 2-s n and m are an integer ≥0 with 2 ≤n+m ≤8; and

Het is a heterocyclic ring, which preferably has 5 members and is selected from the group consisting of thiophene, thiazole, isothiazole, pyrrole, and, particularly preferably, pyrazole, and which may carry 1 or 2 identical or different substituents R1;

as well as pharmaceutically acceptable salts and derivatives of said arylalkyl-or aryloxyalkyl-substituted oxirane carboxylic acid.

Preferred derivatives are the alkyl esters of the arylalky- and aryloxyalkyl-substituted oxirane carboxylic acids, especially the ethyl esters.

Particularly useful inhibitors which fall under formula I above are 2-(6-(4-chlorophenoxy)hexyl)oxirane-2-carboxylic acid ethyl ester (Etomoxir), 2-(6-(4-difluoromethoxyphenoxy)hexyl)-oxirane-2-carboxylic acid ethyl ester, 2-(5-(4-difluoromethoxyphenoxy)pentyl)-oxirane-2-carboxylic acid ethyl ester, and 2-(5-(4-acetylphenoxy)pentyl)-oxirane-2-carboxylic acid ethyl ester, Etomoxir being especially preferred.

Other useful CPT-1 inhibitors are sodium-2-(5-(4-chlorophenyl)pentyl)-oxirane-2-carboxylate (Clomoxir), Perhexyline, sodium-4-hydroxyphenylglycine (Oxfenicine), 2-tetradecylglycidate (TDGA), Palmoxirate, Amiodarone, and derivatives thereof (Deschamps D et al., *Hepatology* 1994 April; 19(4):948-61; Kennedy J A et al., *Biochem Pharmacol* 1996 Jul. 26; 52(2):273-80; Carregal Metal., *Arch Physiol Biochem* 1995 April; 103(1):45-9; Kennedy J A et al., *J Cardiovasc Pharmacol* 2000 December; 36(6):794-801; Swithers S E, *Am J Physiol* 1997 November; 273(5 Pt2): R1649-56; Friedman M I et al., *Am J Physiol* 1990 January; 258(1 Pt 2):R216—21; Seitelberger R et al., *J Clin Chem Clin Biochem* 1990 May; 28(5):341-6; Reinauer H et al., *J Clin Chem Clin Biochem* 1990 May; 28(5):335-9; Skorin C et al., *Biochem J* 1992 Jan. 15; 281(Pt 2):561-7; Tuman R W et al., *Int J Biochem* 1988; 20(2):155-60).

Furthermore, CPT-1 inhibition can be achieved by use of a factor which increases intracellular levels of Malonyl-CoA, since Malonyl-CoA is a physiologic inhibitor of CPT-1 (Prip-Buus C et al., *Biochem J* 1990 Jul15; 269(2):409-15; Winder W W, *Exerc Sport Sci Rev* 1998; 26:117-32; Lopaschuk G D & Gamble J, *Can J Physiol Pharmacol* 1994 October; 72(10): 1101-9).

Consequently, in a preferred embodiment, the inhibitor is a factor which increases the Malonyl-CoA-levels in the patient or the subject which is to be treated.

Suitable factors for increasing the Malonyl-CoA level can be preferably selected from the group consisting of an activator of the Acetyl-CoA-Carboxylase, an inhibitor of the AMP-Kinase, an inhibitor of the Citrate synthase, an inhibitor of the Fatty Acid Synthase or an inhibitor of the Malonyl-CoA-Decarboxylase. Cerulenin as well as the compound C75 are known to be Fatty Acid Synthase inhibitors causing an increase in Malonyl-CoA-levels (Pizer E S et al., *Cancer Research* 60, 213-218, Jan. 15, 2000; Thupari J N et al., *Biochem Biophys Res Commun* 2001 Jul. 13; 285(2):217-23).

Furthermore, the CPT-1 inhibitor may be an antisense oligonucleotide or a dominant negative mutant of the CPT-1 enzyme. Besides antisense oligonucleotides and dominant negative mutants the CPT-1 enzyme, also ribozymes and dsRNA can be used as the CPT-1 inhibitors in the context of the present invention. Furthermore, any combination of one or more antisense oligonucleotide, ribozyme and/or dsRNA with one or more antisense oligonucleotide, ribozyme and/or dsRNA can be used according to the present invention.

The effect of antisense oligonucleotides, ribozymes and dsRNA is due to sequence-specific interactions with the RNA coding for the respective protein. Thereby the structure and/or function of coding RNA sequences are modified in a way that the expression of the originally encoded protein or the effect of the RNA is decreased or completely blocked. Furthermore, this mechanism results in an enzymatic degradation of the mRNA. Thus, those mechanisms work on the basis of inhibiting the production of the target protein itself rather than blocking its function.

As mentioned above, the present invention is based on the finding that a number of neurological an mental disorders which are caused by delipidation of neural tissue and in particular myelin sheets, and that CPT-1 is significantly up-regulated in various tissue from patients suffering from a number of mental and neurological disorders. Disorders which can be treated with CPT-1 inhibitors according to the invention are particularly mental and/or a behavioural disorder.

Thus, in one embodiment the disorder is an organic, including symptomatic, mental disorder. This term comprises a range of mental disorders grouped together on the basis of their having in common a demonstrable etiology in cerebral disease, brain injury, or other insult leading to cerebral dysfunction. The dysfunction may be primary, as in diseases, injuries, and insults that affect the brain directly and selectively; or secondary, as in systemic diseases and disorders that attack the brain only as one of the multiple organs or systems of the body that are involved.

More specifically, the organic mental disorder may for example be selected from dementia, including dementia in Alzheimer's disease and vascular dementia. In more specific embodiments, the disorder is impairment of recent memory and impairment of remote memory.

It is also within the scope of the invention that the CPT-inhibitor according to the invention may be used for treating mental and/or behavioural disorder which are due to psychoactive substance use. More specifically disorders resulting from the use of a psychoactive substance such as alcohol, opioids, cannabinoids, cocaine, caffeine, hallucinogens, tobacco, volatile solvents and multiple drug use.

In a further embodiment, the CPT-1 inhibitor according to the invention is useful for treating and/or preventing mood disorders, including Manic episode, Bipolar affective disorder, Depression, Depressive episode, Recurrent depressive disorder and Persistent mood disorders such as Cyclothymia and Dysthymia.

In a further embodiment, the disorder is neurotic, stress-related and somatoform disorders, including Phobic anxiety disorders such as Panic disorder, Obsessive-compulsive disorder, Reaction to severe stress and adjustment disorders, Dissociative conversion disorders and Somatoform disorders.

In a further aspect of the invention, the CPT-1 inhibitor according to invention may be used for treating and/or preventing disorders which are behavioural syndromes associated with physiological disturbances and physical factors, including disorders selected from Nonorganic sleep disorders, Sexual dysfunction and Eating disorders such as Anorexia nervosa and Bulimia nervosa.

In a further aspect of the invention the disorder is disorders of adult personality and behaviour, such as Paranoid personality disorder, Schizoid personality disorder, Dissocial personality disorder, Emotionally unstable personality disorder, Histrionic personality disorder, Anankastic personality disorder, Anxious personality disorder, Dependent personality disorder, Habit and impulse disorders such as Pathological gambling, Pathological fire-setting, Pathological stealing and Trichotillomania.

In a further aspect of the invention, the disorder is mental retardation, including mild, moderate, severe and profound mental retardation.

In another aspect of the invention, the CPT-inhibitor may be used for treating diseases of the nervous system, including the disorders multiple sclerosis and autoimmune neuropathies.

Further disorders which can be treated according to the invention are, for example, Guillian-Barré, encephalomyelitis, Senile plaque, brain tumors i.e. glioblastoma multiforme, Huntingdon disease, Lou Gehrig's disease, pain, chronic pain, myastemia gravis, Sjogren's syndrome, Tourette syndrome, peripheral neuropathy, occipital neuralgia, motor neurone disease, meningitis, Chronic Lyme's disease, Encephalitis, Schilder's disease or diffuse myelinoclastic sclerosis, Chronic Inflammatory Demyelinating Polyneuropathy, Cerebral atrophy, Acute disseminated encephalomyelitis, Attention-deficit hyperactivity disorder, Cataplexy, Fibromyalgia, General anxiety disorder, Hypersexuality, Impulse-control disorders, Narcolepsy, Obsessive-compulsive disorder, Panic disorder, Posttraumatic stress disorder, Premenstrual dysphoric disorder, Social phobia, Chronic pain, Intermittent explosive disorder, Substance abuse and addiction (including alcoholism).

In a further aspect of the invention there is provided a method of preventing and/or treating disorders caused by delipidation of neural tissue, by administering a Carnitin-Palmitoyl-Transferase-1 (CPT-1) inhibitor to a patient in need thereof in a pharmacologically effective amount.

As used herein, a "pharmaceutically effective amount" of a CPT-1 inhibitor is an amount effective to achieve the desired physiological result, either in cells treated in vitro or in a subject treated in vivo. Specifically, a pharmaceutically effective amount is an amount sufficient to inhibit, for some period of time, one or more clinically defined pathological effects associated with disorders caused by delipidation of neural tissue. The pharmaceutically effective amount may vary depending on the specific CPT-1 inhibitor selected, and is also dependent on a variety of factors and conditions related to the subject to be treated and the severity of the disease. For example, if the inhibitor is to be administered in vivo, factors such as age, weight, sex, and general health of the patient as well as dose response curves and toxicity data obtained in pre-clinical animal tests would be among the factors to be considered. If the CPT-1 inhibitor is to be contacted with cells in vitro, one would also design a variety of pre-clinical in vitro studies to assess parameters like uptake, half-life, dose, toxicity etc. The determination of a pharmaceutically effective amount for a given agent (inhibitor) is well within the ability of those skilled in the art. Preferably, the inhibitor is present in a concentration of 0.01 to 50% per weight of the pharmaceutical composition, more preferably 1 to 30%.

Administration to an individual or patient may be in a single dose or in repeated doses. Repeated doses are preferred, especially once or twice a day until the symptoms disappear or diminish considerably.

The patient to be treated with the methods of the present invention is preferably human. However, also animals, preferably mammals as horses, bovines, dogs or cats and more preferably primates can be treated according to the present invention.

The administration of the CPT-1 inhibitor is not limited to a specific route. Preferred routes of administration to an individual include but are not limited to systemic, parenteral, especially dermal, intradermal, intracutaneous, percutaneous, subcutaneous, topical or transdermal application. In this context, a systemic application is an application which results in a distribution of the CPT-1 inhibitor throughout the body.

The CPT-1 inhibitor may be administered topically. The CPT-1 inhibitor may be administered in the form of salves, creams, emulsions, milks, ointments, powders, tablets, impregnated pads, solutions, gels, sprays, lotions or suspensions. Moreover, the inhibitor may be administered in the form of shampoo, conditioner, hair tonic, hair spray, hair foam, hair paste or fixature. Same can also be administered in the form of lipid or polymeric microspheres or nanospheres or vesicles or of polymeric patches and hydrogels which permit controlled release.

In a further embodiment said prevention and/or treatment of disorder according to the invention comprises the administration of CPT-1 inhibitor in combination with a further therapy. This may result in an additive or even synergistic effect. Without being bound to any theory, the reason for the additive or synergistic effect might be that each therapeutic mean has its own mechanism, and the combination of different mechanism results in an additive or synergistic effect.

In the context of the present invention, the CPT-1 inhibitor may be administered as such, e.g. in substantially pure form, or preferably in combination with at least one excipient and/or auxiliary, e.g. with one or more suitable adjuvant(s) and/or one or more pharmaceutically active and/or acceptable carrier(s), diluent(s), filler(s), binder(s), disintegrant(s), lubricant(s), glident(s), coloring agent(s), flavoring agent(s), opaquing agent(s) and plasticizer(s).

Furthermore, the invention relates to a method to investigate the effect of at least one CPT-1 inhibitor in vitro, said method comprising the steps of cultivating cells under conditions essential for cell proliferation, adding of at least one CPT-1 inhibitor to the cells, and monitoring the proliferation rate and signal transduction of the cells. Said cells are preferably neuritis/neurons or dendrocytes, more preferred neurons, especially of human origin.

Moreover, the invention relates to a method to investigate the effect of at least one CPT-1 inhibitor on the neurological status in vivo, said method comprising the steps of administering at least one fatty acid oxidation inhibitor to the neural cells of an affective disorder animal model, and monitoring the neural status, animal functioning.

Appropriate animal models are e.g. described in Brunmark, C., et al, J Neuroimmunol. 2002 September; 130(1-2): 163-72; Lucas G, Rynnar V V, Du J, Mnie-Filali O, Bisgaard C, Manta S, Lambas-Senas L, Wiborg O, Haddjeri N, Pineyro G, Sadikot A F, Debonnel G. Serotonin(4) (5-HT(4)) receptor agonists are putative antidepressants with a rapid onset of action. Neuron. 2007 Sep. 6; 55(5):712-25. Kurnellas M P, Donahue K C, Elkabes S. Mechanisms of neural damage in multiple sclerosis and its animal models: role of calcium pumps and exchangers. Biochem Soc Trans. 2007 November; 35(Pt 5):923-6. Animal Models of Neurological Disease, II: Metabolic Encephalopathies and the Epilepsies Editor(s): Alan A. Boulton, Glen B. Baker, Roger F. Butterworth Series: Neuromethods, Volume No.: 22 Print ISBN: 978-O-89603-2,1-8, Poindron P, Piguet P (eds): AG. New Animal Models of Human Neurological Diseases. BioValley Monogr. Basel, Karger, 2008, vol 2, pp 1-100.

Methods for determining the neural status are known in the art M. P. Tabor, H. B. van der Worp, P. Sodaar, H. Veldman, E. A. J. Joosten, G. Strous, P. R. Bär. An Advanced In Vitro Model to Study Hypoxia/Low Glucose-Induced Neural Cell Damage and Death Annals of the New York Academy of Sciences 825 (1), 267-278 1749-6632 (1997). J. Gartlory A. Kinsner, A. Bal-Price, S. Coecke and R. H. Clothier. Evaluation of a proposed in vitro test strategy using neural and non-neural cell systems for detecting neurotoxicity. Toxicology in Vitro. Volume 20, Issue 8, December 2006, Pages 1569-1581.

The methods of the invention for investigating the effect of the CPT-1 inhibitor on the neural status are especially applicable when the concentration and/or amount of the inhibitor in the pharmaceutical composition should be tested.

In a further aspect the invention relates to a pharmaceutical composition for treating and/or preventing disorders caused by delipidation of neural tissue, comprising at least one CPT-1 inhibitor and at least one excipient and/or auxiliary.

According to a preferred embodiment, the pharmaceutical composition prepared according to the use of the invention is for systemic or topic administration. The pharmaceutical compositions according to the invention for the topical route can be provided in the form of salves, creams, emulsions, milks, ointments, powders, impregnated pads, solutions, gels, sprays, lotions or suspensions. Moreover, the pharmaceutical compositions according to the invention can be provided in the form of shampoo, conditioner, hair tonic, hair spray, hair foam, hair paste or fixature. Same can also be provided in the form of lipid or polymeric microspheres or nanospheres or vesicles or of polymeric patches and hydrogels which permit controlled release. However, also the other routes of administration disclosed above for the method of the invention apply here.

According to a further preferred embodiment, said pharmaceutical composition further comprises at least one additional active ingredient.

Preferably, said further active ingredient is selected from the group comprising inhibiting hormones or HMGCoA reductases, such as, for example statins like prolactin or somatostatin and chalones (mitotic inhibitors); especially mevastatin, lovastatin, simvastatin, pravastatin, fluvastatin and cerivastatin; fibrates, such as, for example, fenofibrate; clofibrate; clofibric acid derivatives, such as, for example, etofibrate, etofyllinclofibrate; clofibratanaloga, such as, for example, bezafibrate or gemfibrozil; steroids, especially cortisone, vitamin D or derivatives thereof, vitamin A or derivatives thereof, Vitamin B or derivatives thereof, especially vitamin B12, dithranol, urea, salicylic acid, Mahonia aquifolium, fumaric acid, fumaric acid esters, blockers of arachidonic acid, e.g. ometa-3 fatty acids, antibiotics, antimycotics, immunomodulators, e.g. methotrexate, cyclosporine, Fk506, E-selectin blockers, P-selectin blockers, ICAM blockers, LFA-1 blockers, LFA-2 blockers, LFA-3 blockers, VCAM blockers, and/or TNF blockers, with cytokine inhibitors and T-cell activation inhibitors. The above blockers are e.g. antibodies or competitive inhibitors of E-selectin, P-selectin, ICAM, LFA-1, LFA-2, LFA-3, VCAM or TNF, neurological modifiers i.e., acetylcholine receptor blockers, memantine or derivates thereof, galantamine or derivates thereof, Donezepil or derivates thereof, rivastigmine or derivates thereof, .beta nicotinamide adenine dinucleotide or derivates thereof, 5-Hydroxytryptamine (5-HT) Reuptake Inhibitor, Adenosine A1 Receptor (ADORA1) Antagonist, Dopamine Reuptake Inhibitor, Estrogen Receptor 2 (ESR2) Agonist, Phosphodiesterase-4 (PDE-4) Inhibitor, Corticotropin-Releasing Factor Receptor 1 (CRFR1) Antagonist, Corticotropin-Releasing Factor Receptor 1 (CRFR1) Antagonist, Monoamine Oxidase B (MAO-B) Inhibitor, Norepinephrine Reuptake Inhibitor, 5-Hydroxytryptamine (5-HT) Reuptake Inhibitor, cannabinoid receptor inhibitor.

According to a preferred embodiment, the pharmaceutical composition prepared according to the use of the invention comprises further auxiliaries and/or excipients as defined above.

The pharmaceutical composition according to the invention may comprise pharmaceutically acceptable salt forms of further active compounds and standard pharmaceutical formulation techniques are well known to persons skilled in the art. Usually, the inhibitor is formulated with one or more pharmaceutically acceptable additives or auxiliary substances, such as physiological buffer solution, e.g. sodium chloride solution, demineralized water, stabilizers, such as protease or nuclease inhibitors, preferably aprotinin, ε-aminocaproic acid or pepstatin A or sequestering agents such as EDTA, gel formulations, such as white vaseline, low-viscosity paraffin and/or yellow wax, etc. depending on the kind of administration.

Suitable further additives are, for example, alcohols, such as, for example, isopropanol or ethanol; detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The pharmaceutical composition may formulated in a physiological buffer solution which preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the pharmaceutical composition is in general adjusted using a suitable organic or inorganic buffer, such as, for example, preferably using a phosphate buffer, tris buffer (tris(hydroxymethyl)aminomethane), HEPES buffer ([4-(2-hydroxyethyl)piperazino]ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The pharmaceutical composition according to the invention can be administered in a conventional manner, e.g. by means of oral dosage forms, such as, for example, tablets or capsules, by means of the mucous membranes, for example the nose or the oral cavity, in the form of depositories implanted under the skin, by means of injections, infusions or gels which contain the pharmaceutical compositions according to the invention. Furthermore, the treatment can be carried out by means of a transdermal therapeutic system (TTS), which makes possible a temporally controlled release of the pharmaceutical compositions. TTS are known for example, from EP 0 944 398 A1, EP 0 916 336 A1, EP 0 889 723 A1 or EP 0 852 493 A1.

The pharmaceutical composition may be in the form of an injection solution. Injection solutions are in general used if only relatively small amounts of a solution or suspension, for example about 1 to about 20 ml, are to be administered to the body. Infusion solutions are in general used if a larger amount of a solution or suspension, for example one or more liters, are to be administered. Since, in contrast to the infusion solution, only a few milliliters are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

In one embodiment the pharmaceutical composition according to the invention is a formulation in the form of a gelatine capsule, wherein the capsule e.g. contains a solution of the inhibitor in a mixture of middle chain triglycerides (for example Miglyol 812) or another diluent, in an amount of 20% to 30%, preferably 20% to 25%, more preferably 20.2%.

When the pharmaceutical composition is to be administered topically, preferably said at least one excipient and/or auxiliary is hydrophobic and is preferably selected from the group comprising petroleum jelly, wax, oleyl alcohol, propylene glycol monostearate, propylene glycol monopalmitostearate, isopropyl laureate, isopropyl myristate, isopropyl palmitate, isopropyl stearate, ethyl myristate, propyl myristate, butyl myristate, ethyl oleate, cetylstearyl alcohol, Vaseline, lanolin alcohol or paraffin oil.

In a further aspect, the invention relates to the use of a Carnitin-Palmitoyl-Transferase-1 (CPT-1) inhibitor for the preparation of a pharmaceutical composition for use in treating and/or preventing disorders caused by delipidation of neural tissue. The CPT-1 inhibitor may in useful embodiments be as defined above. The disorders are as defined above.

In a further aspect the invention relates to a method for the production of a pharmaceutical composition for treating and/or preventing disorders caused by delipidation of neural tissue, comprising the step of mixing at least one CPT-1 inhibitor with at least one excipient and/or auxiliary.

The present invention provides efficient pharmaceutical compositions and methods for the treatment of disorders caused by delipidation of neural tissue. Consequently, the present invention represents a veritable progress in that medical field.

The following examples and tables are intended to illustrate the present invention without limiting the scope of the claims.

EXAMPLES

Example 1

Y-Maze Short Term Memory Test

Animals

Male Wistar rats were purchased from Taconic, Denmark. Animal weight was close to 300 g. The animals were singly housed. Food and water was available ad libitum.

Description

Spontaneous alternation. A Y-maze was used to assess (without food deprivation or other aversive procedures) the normal navigation behaviors of rodents. Naive rats are placed in a Y-shaped maze as shown in FIG. 1 for 5 to 8 min. All arm entries are sequentially scored so that the total number of arm entries, as well as the sequence of entries, are recorded. Data are analyzed to determine the number of arm entries without repetition. Success in this test is indicated by a high rate of alternation in the control groups indicating that the animals can remember which arm was entered last.

On the day of testing, the rats are given subcutaneous injection of either vehicle (n=9), 0.1 mg/kg MK-801 (n=8) or 0.1 mg/kg MK-801 (also known as Dizocilpine) and the CPT-1 inhibitor Etomoxir 1 mg/kg (1 mg/ml etomoxir ester dilution in olive oil, n=5) 1 hour before the testing (to avoid the MK-801 induced hyperactivity).

Figure 2:
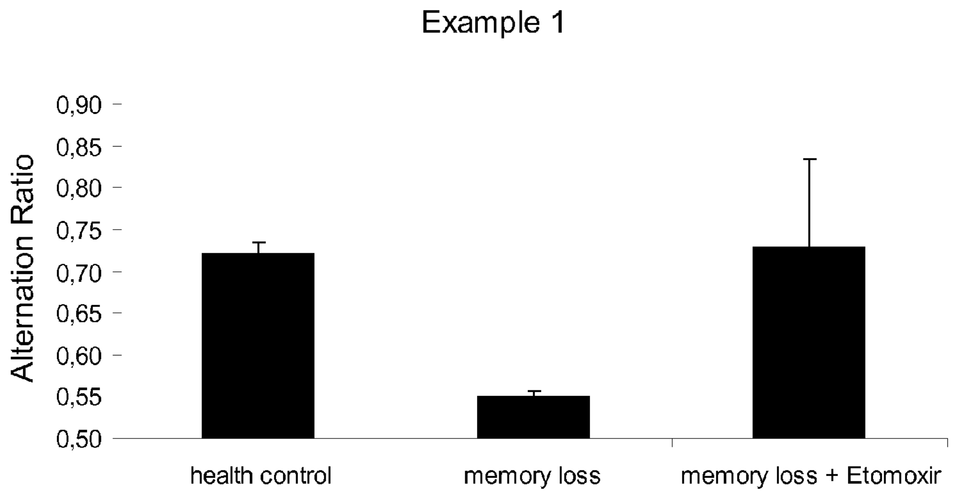
FIG. 2 is a bar chart showing the effects of Etomoxir on short term memory restoration.

As can be seen in FIG. 2, one subcutaneous injection of Etomoxir is able to restore the loss of short term memory that is induced. Sixty percent of the animals had nearly perfect memory (scores of 92-100%). The highest scores in the normal animal group was 88% in the MK-801+vehicle treated animals the highest score were 66%. This indicates that Etomoxir not only restores short term memory loss it can also improve short term memory compared to normal healthy individuals.

Example 2

Passive Avoidance Test (Long Term Memory)

Animals

Male Wistar rats were purchased from Taconic, Denmark. Animal weight was close to 300 g. The animals were singly housed. Food and water was available ad libitum.

Setup of the Experiment

In order to test long term memory, a passive avoidance apparatus was used. The passive avoidance apparatus consist of 2 compartments: a white compartment and a black compartment, which are separated by guillotine doors. There is a lamp hanging 10 cm above the white compartment and there is a lid covering the black compartment. The black compartment contains a stainless steel grid floor.

The test was performed in the lab where the rats normally live, and all the rats were present in the room all the time during the experiment. The apparatus was placed a little bit above the floor on 2 cages. The electrical current strength was adjusted to 0.36 mA and the duration was 5 sec. The general light in the room was switched off, there was one desk lamp and the lamp above the white compartment that were switched on. All the rats are weighted one day before the experiment, the concentration of MK-801 per mean body weight is calculated and the dilutions are prepared Day 1: Training The rats are given subcutaneous injection of either vehicle (n=4), 0.1 mg/kg MK-801 (n=8) or 0.1 mg/kg MK-801 and etomoxir 1 mg/kg (1 mg/ml etomoxir ester dilution in olive oil, n=10) 1 hour before the training (to avoid the MK-801 induced hyperactivity). The rat is placed in the white compartment facing the wall opposite to guillotine doors. After 20 sec the doors are lifted and the time to enter the black compartment is measured. When animal enters the black compartment with all 4 feet, the electric shock is delivered and then the rat is immediately removed from the apparatus.

Day 2: Testing

Twenty-four hours after the training, a retention test is performed to determine long-term memory. The animal is placed in the light compartment. After 20 seconds the guillotine doors are opened, and the time latency for entering into the shock compartment as well as the time spent in the black compartment is measured. The test session ends when the animal enters the shock compartment or remains in the light compartment for more than 300 s. During this session, no electric shock is applied.

Figure 3:
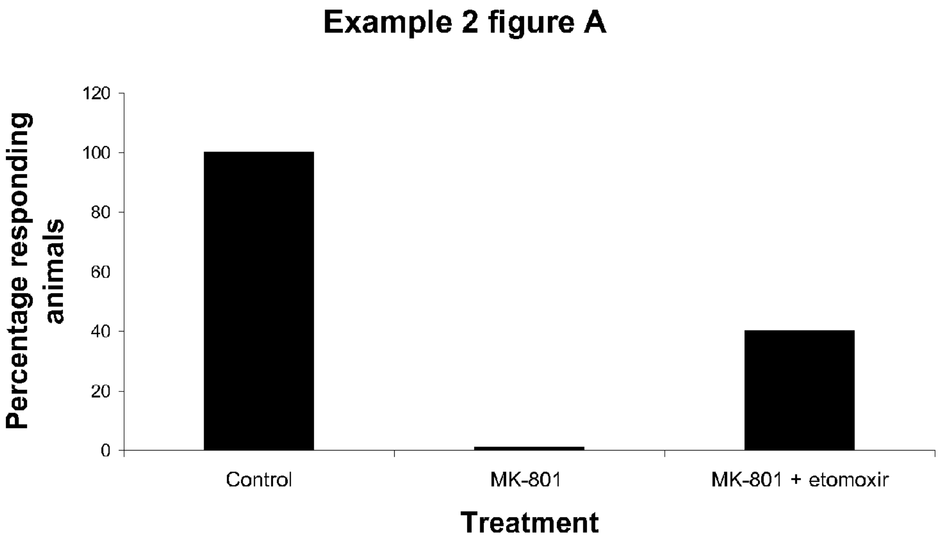
FIG. 3 is a bar chart showing the effects of Etomoxir on long term memory restoration.
Figure 4:
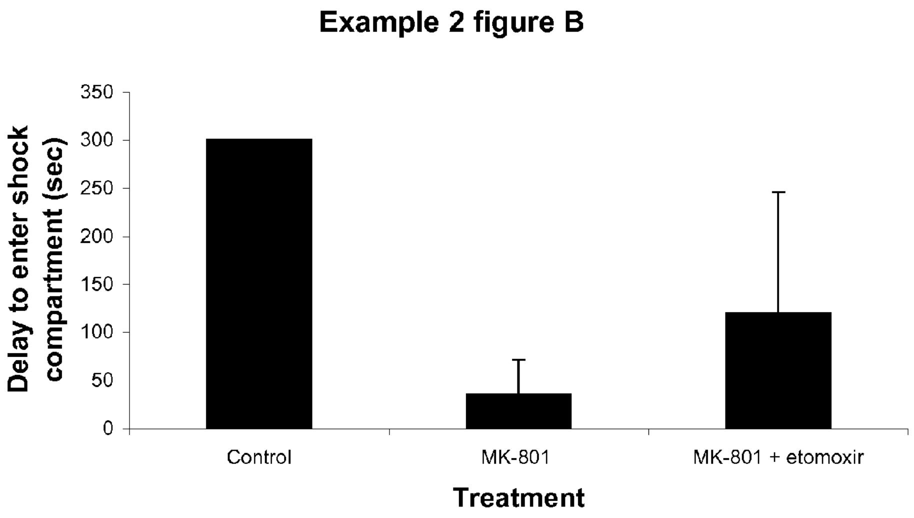
FIG. 4 is a bar chart showing the average time that animals in different groups stayed in a light compartment.

As can be seen in FIGS. 3 and 4, one subcutaneous injection of Etomoxir is able to restore the loss of long term memory in 40% of the animals. None of the MK-801 treated had measurable long term memory. In the vehicle treated group 100% long term memory was measured. The percentage of animals that had long term memory is depicted in FIG. 3. In FIG. 4 the average time is shown that the animals in the different groups stayed in the light compartment. The experiment was stopped after 300 seconds.

Example 3

The Chronic Mild Stress (CMS) Model of Depression

For a prolonged period rats are submitted to a succession of mild stressors. Consequently rats enter a depression-like state (anhedoina), however, upon concomitant treatment with antidepressants a fraction of rats recovers over time (Jayatissa et al., 2006). Time point of onset of antidepressant action correlates well to therapeutic action in the clinic and also drug efficacy, measured as a reduction in number of rats resistant to drug treatment, is addressed in the model.

Animals

Male Wistar rats were purchased from Taconic, Denmark. Animal weight was close to 200 g when adaptation for sucrose consumption was initiated, and approximately 350 g at the start of stress regime. The animals were singly housed, except when grouping was applied as a stress parameter. Food and water was available ad libitum except when food or/and water deprivation was applied as a stress parameter. The standard 12-h light/dark cycle was only changed in course of stress regime.

Sucrose Consumption Test

The animals were first trained to consume a palatable sucrose solution (1.5%). The training lasted 5 weeks. In this period the sucrose test was made twice a week during the first 3 weeks and once a week during the last two weeks. Animals were food and water deprived 14 hours before the test. The test consisted of 1-hour exposure to a bottle with sucrose solution. During the stress period the sucrose consumption test was performed once a week.

Chronic Mild Stress Protocol

On the basis of sucrose intakes in the 3 final baseline tests, the animals were divided into 2 matched groups and placed in separate rooms. One group was exposed to an initial 3 weeks of chronic mild stressors and the other was left undisturbed. The unchallenged group was food and water deprived 14 h before sucrose consumption test, otherwise food and water was freely available.

The stress procedure was optimized in the laboratory of Ove Wiborg in Aarhus, Denmark. The stress protocol was slightly modified from the protocol published by Papp (Sánchez C, Gruca P, Bien E, Papp M. R-citalopram counteracts the effect of escitalopram in a rat conditioned fear stress model of anxiety. Pharmacol Biochem Behav. 2003 July; 75(4):903-7).

The stress protocol consisted of 1 period of intermittent illumination, stroboscopic light, grouping, food or water deprivation; 2 periods of soiled cage and no stress; 3 periods of 45° box tilting. During grouping rats were housed in pairs with different partners alternately being a resident or intruder. All the stressors lasted from 10 to 14 h. After the initial 3 weeks of exposure to stress, the unchallenged and stress groups were divided each into 2 matched subgroups (based on sucrose intake) and subjected to chronic Etomoxir treatment (4 mg/kg etomoxir in oil via intra peritoneal injection (i.p.) daily (n=10 non stressed animals, n=20 stressed animals)) or vehicle administration (oil i.p. injection daily (n=8 non stressed animals, n=10 stressed animals)). Stress was continued during the entire period of treatment. Percentage well being is calculated as follows:

Test=Average Sucrose consumption animals in test group

Control=Average Sucrose used animal control group

Percentage well being=(Test/control)×100%

Figure 5:
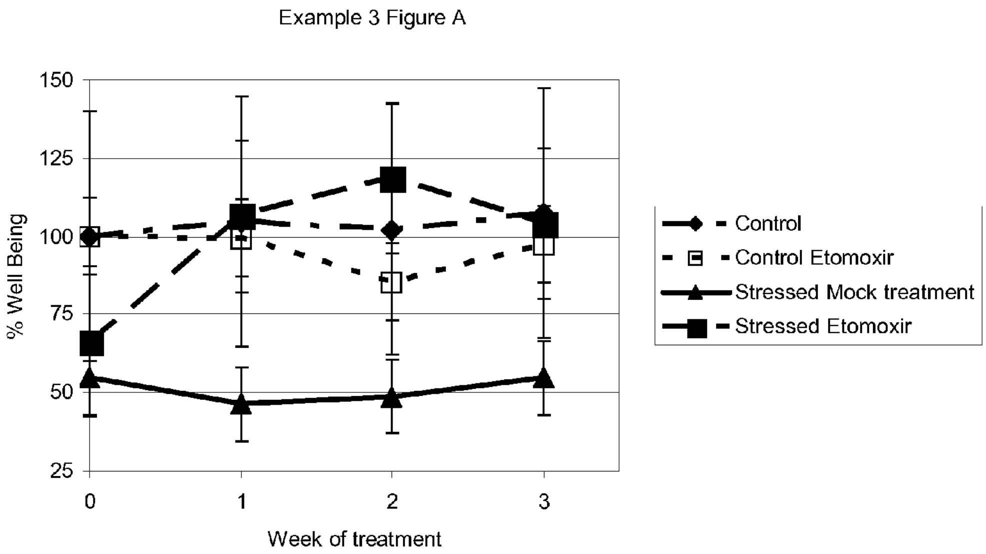
FIG. 5 is a graph showing the well being of animals treated with Etomoxir over time.
Figure 6:
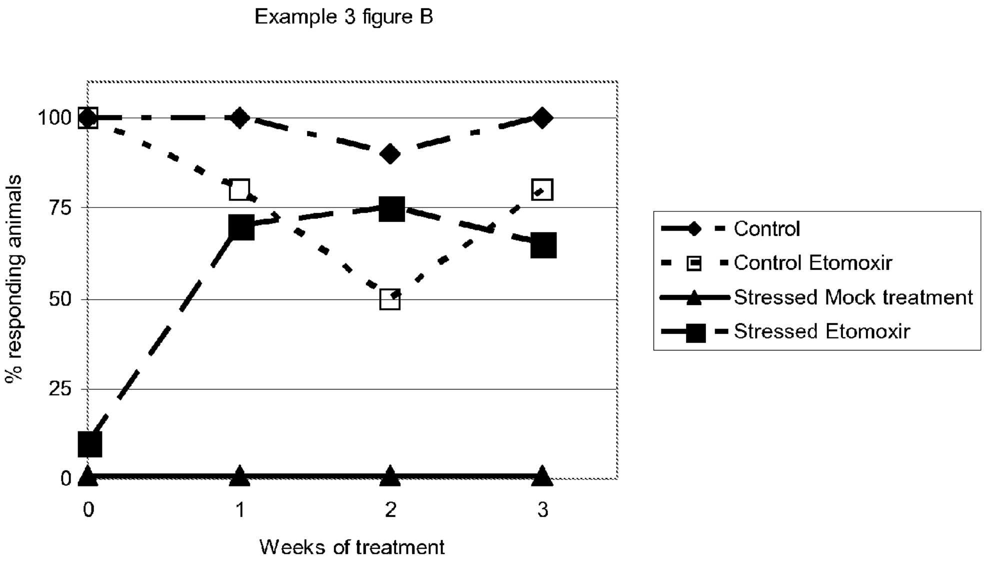
FIG. 6 is a graph showing animal responses to treatment over time.

The results of this experiment are depicted in FIGS. 5 and 6. As can be seen in FIG. 5 the animals treated with Etomoxir were responding like normal non-depressed animals within 1 week of treatment (earliest time point measured), where the depressed group did not respond.

In FIG. 6 it can be seen that about 70% of the animals responded to the treatment. An animal is registered as responding when it consumed at least 90% of the amount of sucrose that the animal consumed before stress was applied to it.

Example 4

Determination of CPT-1 Expression in Various Tissues

For determination of CPT-1 expression in various tissues of diseased individuals versus healthy individuals (controls), the Gene Logic Technology was used. Especially, the following steps were performed:

Tissue Handling

Tissue was snap frozen in liquid $N_2$ and stored in large metal tanks continuously filled with liquid $N_2$. Once selected for processing, each tissue was crushed in a freezer mill into a fine powder to more effectively handle the tissue for RNA extraction.

RNA Extraction and QC

Total RNA was extracted using a Trizol method and an RNeasy column. RNA quality was assessed using a combination of a 260/280 ratio and assessment from the Agilent LabChip™ cDNA Synthesis and Labeling cDNA was synthesized using T7-$(dt)_{24}$oligos and SuperScript II RT followed by T4 Polymerase and was purified using Phase Lock Gel (PLG) and Phenol: Chloroform extraction. Labeling was carried out using biotinylated CTP in an In-Vitro transcription reaction. Labeled product, cRNA, was cleaned up using RNeasy columns, analyzed on gel and assessed by 260/280 ratio. cRNA was then fragmented and these fragments were analyzed using the Agilent LabChip™.

Hybridization and Processing

CRNA was analyzed using the latest version of the Affymetrix U-133 GeneChip. Approximately 10 μg of cRNA was used per GeneChip®. Hybridization and washing were carried out in strict accordance to Affymetrix's established protocols.

Image Analysis and Normalization

GeneChips were scanned under low PMT, and image quality was subject to strict quality control protocols using proprietary Gene Logic algorithms. Data were normalized using either Affymetrix MAS 4.0 or MAS 5.0 algorithms. In addition, "spike-ins" were employed for most samples to construct a standard curve and obtain RNA concentration values expressed in parts per million.

The results are summarized in the below Tables 1 and 2. Table 1 contains the simple data, while Table 2 shows the respective mean values plus standard deviation.

TABLE 1

| Description | Experimental Sample | Expression compared to control (%) | Mean % CPT1 Up-regulation | Standard Deviation |
|---|---|---|---|---|
| INFERIOR TEMPORAL GYRUS (BRODMANN AREA 20), COCAINE ABUSE | INFERIOR TEMPORAL GYRUS (BRODMANN AREA 20), COCAINE ABUSE | 143 | 143 | 25.44 |
| INFERIOR TEMPORAL GYRUS (BRODMANN AREA 20), COCAINE ABUSE | | 136 | | |
| INSULA, COCAINE ABUSE | | 178 | | |
| MIDDLE TEMPORAL GYRUS (BRODMANN AREA 21), COCAINE ABUSE | | 122 | | |
| CEREBELLAR HEMISPHERE, COCAINE ABUSE | | 216 | | |
| CEREBELLAR HEMISPHERE, COCAINE ABUSE | | 120 | | |
| CINGULATE GYRUS (BRODMANN AREA 23), COCAINE ABUSE | | 136 | | |
| CORPUS CALLOSUM, COCAINE ABUSE | | 141 | | |
| CORPUS CALLOSUM, COCAINE ABUSE | | 140 | | |
| DORSAL RAPHE, COCAINE ABUSE | | 125 | | |
| FRONTAL POLE (BRODMANN AREA 10), COCAINE ABUSE | | 132 | | |
| FRONTAL POLE (BRODMANN AREA 10), COCAINE ABUSE | | 124 | | |
| HIPPOCAMPUS, COCAINE ABUSE | | 148 | | |

TABLE 1-continued

| Description | Experimental Sample | Expression compared to control (%) | Mean % CPT1 Up-regulation | Standard Deviation |
|---|---|---|---|---|
| MOTOR CORTEX (BRODMANN AREA 4), COCAINE ABUSE | | 191 | | |
| MOTOR CORTEX (BRODMANN AREA 4), COCAINE ABUSE | | 133 | | |
| NUCLEUS BASALIS, COCAINE ABUSE | | 142 | | |
| NUCLEUS BASALIS, COCAINE ABUSE | | 127 | | |
| SUPERIOR TEMPORAL GYRUS (BRODMANN AREA 22), COCAINE ABUSE | | 121 | | |
| THALAMUS, COCAINE ABUSE | | 137 | | |
| CINGULATE GYRUS (BRODMANN AREA 29), SUICIDE WITH HISTORY OF DEPRESSION | CINGULATE GYRUS (BRODMANN AREA 29), SUICIDE WITH HISTORY OF DEPRESSION | 126 | 143 | 13.21 |
| CINGULATE GYRUS (BRODMANN AREA 29), SUICIDE WITH HISTORY OF DEPRESSION | | 153 | | |
| INFERIOR TEMPORAL GYRUS (BRODMANN AREA 20), SUICIDE WITH HISTORY OF DEPRESSION | | 159 | | |
| MIDDLE TEMPORAL GYRUS (BRODMANN AREA 21), SUICIDE WITH HISTORY OF DEPRESSION | | 136 | | |
| MIDDLE TEMPORAL GYRUS (BRODMANN AREA 21), SUICIDE WITH HISTORY OF DEPRESSION | | 141 | | |

TABLE 2

| Experimental Sample | Mean % CPT-1 up-regulation | Standard deviation |
|---|---|---|
| SENILE PLAQUE | 163 | 36 |
| Brain COCAINE ABUSE | 143 | 25 |
| Brain, SUICIDE WITH HISTORY OF DEPRESSION | 143 | 13 |

The invention claimed is:

1. A method of treating disorders caused by delipidation of neural tissue, wherein the disorders are primary disorders which affect the brain directly and selectively and which are selected from the group consisting of multiple sclerosis, mental and/or behavioural disorder which are caused by psychoactive substance use, schizoid personality disorder, depression, depressive episode, recurrent depressive disorder, persistent mood disorder, mental retardation and impairment of memory and which are not secondary disorders wherein the brain is attacked as one of multiple organs of the body by administering to a patient a Carnitin-Palmitoyl-Transferase-1 (CPT-1) inhibitor in a pharmacologically effective amount, whereby the CPT-1 inhibitor is an aryloxyalkyl-substituted oxirane carboxylic acid of the following formula I

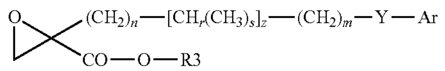

wherein

Ar is a substituted phenyl radical

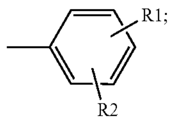

R1 is a hydrogen atom;

R2 is a hydrogen atom, a halogen atom, or a 1-4 C lower alkyl group; a 1-4 C lower alkoxy group, a nitro group, a trifluoromethyl group, a fully or predominantly fluorine-substituted 1-3 C alkoxy group or

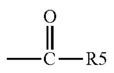

R3 is a hydrogen atom or a 1-4 C lower alkyl group;

R5 is a 1-4 C lower alkyl group;

Y is the grouping —O—;

z is 0 s is 1 or 2 r is 2-s n and m are integer >0 with 2<n+m<8, and as well as pharmaceutically acceptable salts or derivatives of said aryloxyalkyl-substituted oxirane carboxylic acid.

2. The method according to claim 1, wherein the patient is a human.

3. The method according to claim 1, wherein the disorder is a mental and/or a behavioural disorder caused by psychoactive substance use.

4. The method according to claim 1, wherein said CPT-1 inhibitor is administered systemically or topically.

5. The method according to claim 1, wherein said CPT-1 inhibitor is administered in combination with a further therapy.

6. The method according to claim 1, wherein the inhibitor is administered alone as a substantially pure compound.

7. The method according to claim 1, wherein the inhibitor is administered together with at least one excipient and/or auxiliary.

8. The method according to claim 7, wherein the excipient and/or auxiliary is selected from the group consisting of one or more suitable adjuvant(s), one or more pharmaceutically active and/or acceptable carrier(s), diluent(s), filler(s), binder(s), disintegrant(s), lubricant(s), glident(s), coloring agent(s), flavoring agent(s), opaquing agent(s) and plasticizer(s).

9. The method according to claim 1, wherein said aryloxyalkyl-substituted oxirane carboxylic acid of formula I is 2-(6-(4-chlorophenoxy)hexyl)oxirane-2-carboxylic acid ethyl ester (Etomoxir), 2-(6-(4-difluoromethoxyphenoxy)hexyl)oxirane-2-carboxylic acid ethyl ester, 2-(5-(4-difluoromethoxyphenoxy)pentyl)oxirane-2-carboxylic acid ethyl ester, 2-(5-(4-acetylphenoxy)pentyloxirane-2-carboxylic acid ethyl ester, 2-(6-(4-chlorophenoxy)hexyl)oxirane-2-carboxylic acid, 2-(6-(4-difluoromethoxyphenoxy)hexyl)oxirane-2-carboxylic acid, 2-(5-(4-difluoromethoxyphenoxy)pentyl)oxirane-2-carboxylic acid, or 2-(5-(4-acetylphenoxy)pentyloxirane-2-carboxylic acid.

10. The method according to claim 1, wherein the neural tissue is myelin sheet.

11. The method according to claim 1, wherein the disorder is schizoid personality disorder.

12. The method according to claim 1, wherein the disorder is mental retardation.

13. The method according to claim 1, wherein the mental and/or behavioural disorder which is caused by psychoactive substance use is due to the use of a psychoactive substance selected from alcohol, opioids, cannabinoids, cocaine, caffeine, hallucinogens, tobacco, volatile solvents and multiple drugs.

14. The method according to claim 1, wherein the persistent mood disorder is cyclothymia or dysthymia.

15. The method according to claim 1, wherein mental retardation is mild, moderate, severe or profound mental retardation.

16. The method according to claim 1, wherein the impairment of memory is impairment of recent memory or impairment of remote memory.

* * * * *